US00PP10298P

United States Patent [19]

Cunneen

[11] Patent Number: Plant 10,298

[45] Date of Patent: Mar. 24, 1998

[54] ARGYRANTHEMUM PLANT NAMED 'SUGAR BABY'

[76] Inventor: Thomas M. Cunneen, Private Bag 11, Camden, New South Wales 2570, Australia

[21] Appl. No.: 726,480

[22] Filed: Oct. 7, 1996

[51] Int. Cl.[6] ..... A01H 5/00

[52] U.S. Cl. ..... Plt./68.1

[58] Field of Search ..... Plt./68.1

*Primary Examiner*—Howard J. Locker

*Assistant Examiner*—Kent L. Bell

*Attorney, Agent, or Firm*—C. A. Whealy

[57] ABSTRACT

A distinct cultivar of Marguerite daisy plant named 'Sugar Baby', characterized by its compact plant habit; dense, bushy and freely branching plant form; freely and early flowering; and pure white ray and bright yellow disc florets.

2 Drawing Sheets

The present invention relates to a new and distinct cultivar of Marguerite daisy plant, botanically known as *Argyranthemum frutescens* and referred to by the cultivar name 'Sugar Baby'.

The new cultivar is a product of a planned breeding program conducted by the inventor in Cobbitty, New South Wales, Australia. The objective of the breeding program was to develop compact and freely-flowering Marguerite daisies that flower early.

The new cultivar originated from a cross made by the inventor in 1991 of a seedling selection of *Argyranthemum frutescens* identified as number 90003, as the male or pollen parent, with the *Argyranthemum frutescens* cultivar 'Frosty' (not patented), as the female or seed parent. The cultivar 'Sugar Baby' was discovered and selected by the inventor as a flowering plant within the progeny of the stated cross in a controlled environment in Cobbitty, New South Wales, Australia. Plants of the new Marguerite daisy are more compact than either of its parents.

Asexual reproduction of the new cultivar by terminal cuttings taken in Cobbitty, New South Wales, Australia, and Encinitas, Calif., has shown that the unique features of this new Marguerite daisy are stable and are reproduced true to type in successive propagations.

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Sugar Baby' which distinguish 'Sugar Baby' as a new and distinct cultivar:

1. Compact plant habit.
2. Dense, bushy and freely branching plant form.
3. Numerous inflorescences per plant.
4. Early flowering.
5. Pure white ray and bright yellow disc florets.

The accompanying colored photographs illustrate the overall appearance of the new cultivar showing the colors as true as it is reasonably possible to obtain in colored reproductions of this type.

The first photograph comprises a side perspective view of a typical container plant of 'Sugar Baby'.

The second photograph comprises a close-up view of inflorescences of plants of 'Sugar Baby'. Floret and foliage colors in the photographs may appear different from the actual colors due to light reflectance.

The following observations, measurements, values, and comparisons describe plants grown in Encinitas, Calif., under outdoor conditions. Color references are made to The Royal Horticultural Society Colour Chart except where general terms of ordinary dictionary significance are used.

Botanical classification: *Argyranthemum frutescens* cultivars 'Sugar Baby'.

Parentage:

*Male or pollen parent.*—Seedling selection of *Argyranthemum frutescens*, identified as number 90003.

*Female or seed parent.*—*Argyranthemum frutescens* cultivar 'Frosty' (not patented).

Propagation:

*Type cutting.*—Terminal cuttings.

*Time to initiate and develop roots.*—7 to 10 days at temperatures of 21° C.

*Rooting habit.*—Numerous, fibrous, and freely branching.

Plant description:

*General appearance.*—Upright and compact inverted triangle. Dense and bushy herbaceous plant with bipinnatisect foliage and erect flower stems that hold the inflorescences about 3 cm above the foliage. Appropriate for various sizes of containers.

*Plant height.*—About 16 cm from soil level to top of inflorescences.

*Branching.*—Freely branching, plants do not require pinching.

*Vigor.*—Moderate to vigorous.

*Stem color.*—144A.

*Foliage description.*—Arrangement: Alternate, single. Leaf shape: Bipinnatisect. Leaf apex: Acute. Leaf base: Attenuate. Leaf aspect: Flat. Leaf length: About 5 cm. Leaf width: About 2.7 cm. Leaf texture: Glabrous and smooth. Leaf color: Young and fully expanded leaves: Adaxial surface: 138A. Abaxial surface: 137C. Petiole: 138A. Venation: Adaxial surface: 138A. Abaxial surface: 137C.

Flowering description:

*Inflorescence.*—Single daisy-type composite inflorescence form. Inflorescences form at upper leaf axils. Florets arranged acropetally on a capitulum. Inflorescences last on the plant for 2 to 3 weeks and are persistent.

*Natural flowering season.*—Natural flowering season is spring to early fall. Plants flower continuously during this period.

*Inflorescence diameter.*—About 3 cm.

*Inflorescence depth (height).*—About 8 mm.

*Fragrance.*—None.

*Ray florets.*—Appearance: Satiny. Shape: Elliptic. Apex: Obtuse to dentate. Base: Attenuate. Margin: Entire. Length: About 1.3 cm. Width: About 4 mm. Texture: Smooth, glabrous and longitudinally ribbed. Color: When opening and mature: Abaxial surafce: 155D. Adaxial surface: 155D. Number of ray florets per inflorescence: About 20.

*Disc florets.*—Shape:Tubular, fluted at top. Diameter of disc: About 1 cm. Disc floret length: About 4 mm. Disc floret width: About 1 mm. Color, immature and mature: 14A. Number of disc florets per inflorescence: Numerous, usually more than 50.

*Peduncle.*—Length: First peduncle: About 3 cm. Fourth peduncle: About 4.5 cm. Strength: Strong and erect, inflorescences held about 3 cm above foliage. Diameter: About 2 mm. Texture: Smooth. Color: 144A.

*Flower bud.*—Shape: Spherical and slightly flattened. Length: About 4 mm. Diameter: About 6 mm. Color: Brown.

*Androecium.*—Present only on disc florets. Anther color: Yellow. Pollen color: Yellow. Amount of pollen: Moderate.

*Gynoecium.*—Present on both disc and ray florets. Pistil number: One per floret. Style color: Yellow green. Stigma color: Yellow green.

Disease resistance: No susceptibility nor resistance to fungal, bacterial or viral pathogens has been noted.

Seed production: Seed production is typically not observed.

It is claimed:

1. A new and distinct Marguerite daisy plant named 'Sugar Baby', as illustrated and described.

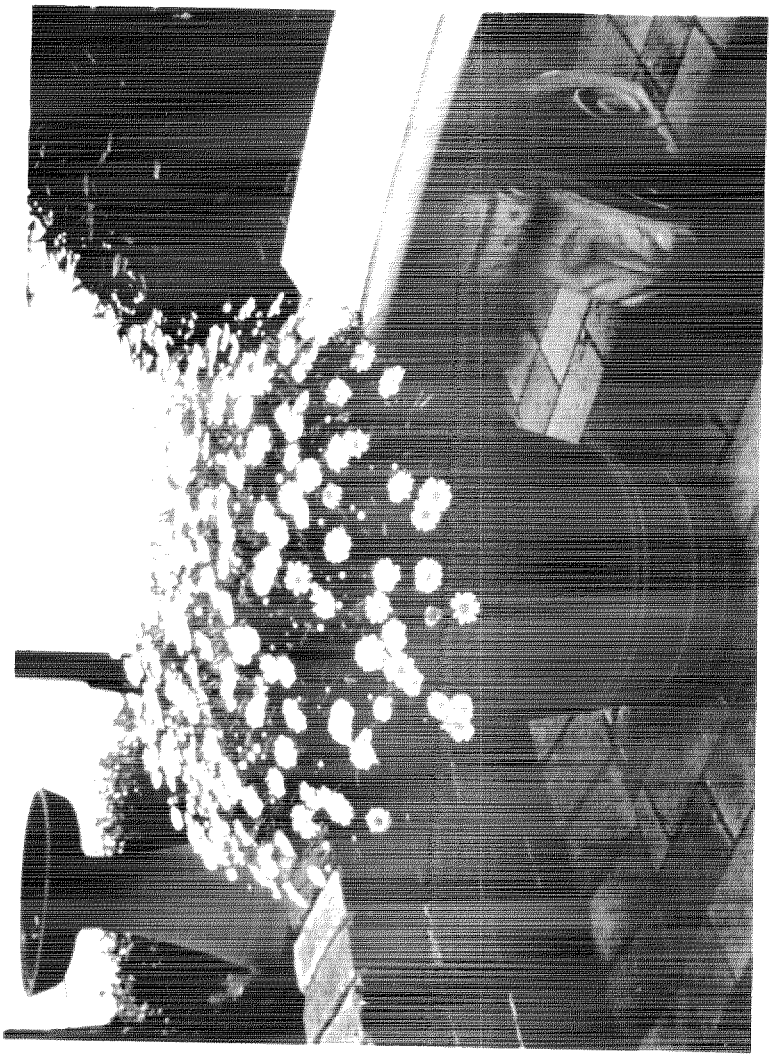

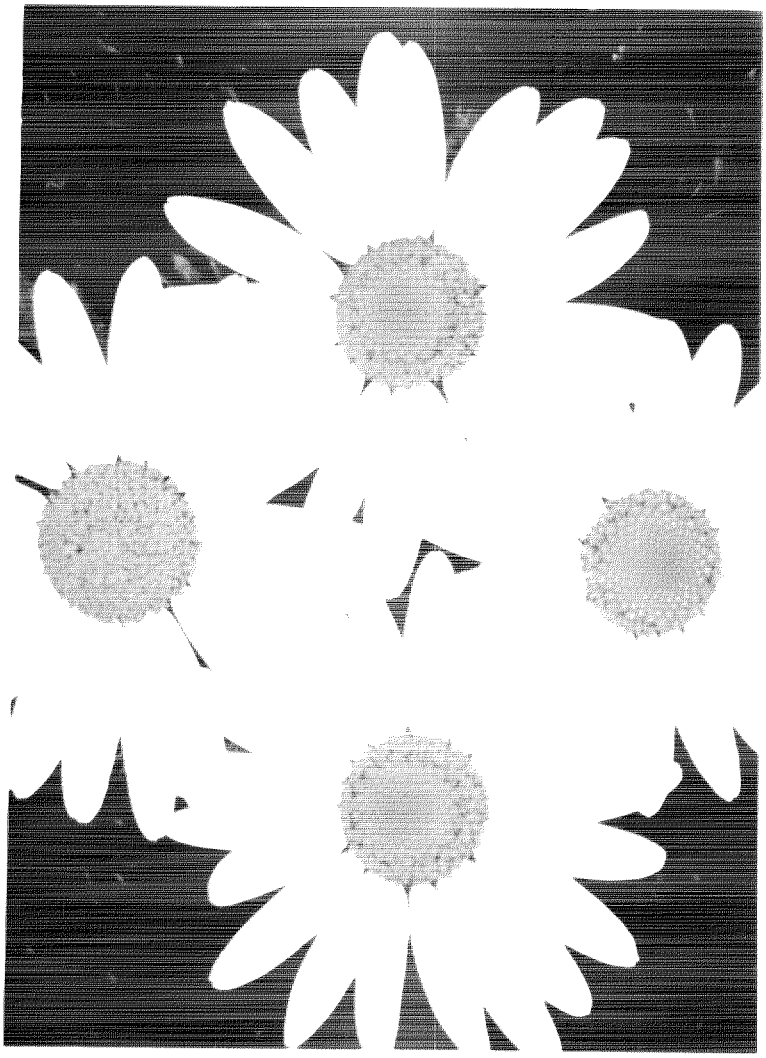

* * * * *